US009351842B2

(12) United States Patent
Todd et al.

(10) Patent No.: US 9,351,842 B2
(45) Date of Patent: May 31, 2016

(54) PROSTHETIC KNEE IMPLANT

(71) Applicant: Zimmer, Inc., Warsaw, IN (US)

(72) Inventors: Dwight Todd, Columbia City, IN (US);
Alex Stoller, Fort Wayne, IN (US);
Aravinda Bobba, Warsaw, IN (US);
Harish Kumar, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 81 days.

(21) Appl. No.: 14/201,240

(22) Filed: Mar. 7, 2014

(65) Prior Publication Data

US 2014/0277537 A1    Sep. 18, 2014

Related U.S. Application Data

(60) Provisional application No. 61/784,521, filed on Mar. 14, 2013.

(51) Int. Cl.
*A61F 2/38*    (2006.01)

(52) U.S. Cl.
CPC ............... *A61F 2/3836* (2013.01); *A61F 2/38* (2013.01); *A61F 2/389* (2013.01); *A61F 2/3859* (2013.01); *A61F 2/3886* (2013.01)

(58) Field of Classification Search
CPC .......... A61F 2/38; A61F 2/3859; A61F 2/389
See application file for complete search history.

(56) References Cited

U.S. PATENT DOCUMENTS

| 5,219,362 | A | 6/1993 | Tuke et al. |
| 5,681,354 | A | 10/1997 | Eckhoff |
| 5,728,162 | A | 3/1998 | Eckhoff |
| 2008/0161918 | A1* | 7/2008 | Fankhauser ............... A61F 2/38 623/14.12 |
| 2009/0319047 | A1* | 12/2009 | Walker ................ A61F 2/3886 623/20.15 |
| 2010/0016978 | A1* | 1/2010 | Williams .............. A61F 2/3868 623/20.27 |
| 2012/0179264 | A1 | 7/2012 | Todd et al. |
| 2012/0323335 | A1* | 12/2012 | Parisi ................... A61F 2/3886 623/20.35 |

(Continued)

FOREIGN PATENT DOCUMENTS

| WO | WO-2012031774 A1 | 3/2012 |
| WO | WO-2013007747 A1 | 1/2013 |

(Continued)

OTHER PUBLICATIONS

"International Application Serial No. PCT/US2014/021955, International Search Report mailed Jun. 2, 2014", 6 pgs.

(Continued)

*Primary Examiner* — Jason-Dennis Stewart
(74) *Attorney, Agent, or Firm* — Schwegman Lundberg & Woessner, P.A.

(57) ABSTRACT

Knee implant systems and methods for implantation or use in a knee joint, are disclosed. A knee implant system can include at femoral component having a femur-contacting surface and an opposing articulation surface, and proximal, distal, anterior and posterior portion. The femoral component can include a medial condyle and a lateral condyle, where each of the condyles define respective distal-most points and have substantially equal widths. The width of each of the condyles can define respective condyle midpoints, where the distal-most points can be located laterally from the midpoints. The femoral component can include a trochlear groove that can define a distal-most sulcus point located halfway between the distal-most point of the medial condyle and the distal-most point of the lateral condyle.

24 Claims, 10 Drawing Sheets

(56) References Cited

U.S. PATENT DOCUMENTS

| | | | | | |
|---|---|---|---|---|---|
| 2012/0323336 | A1* | 12/2012 | Parisi | ............... | A61F 2/3886 623/20.35 |
| 2013/0245777 | A1* | 9/2013 | Jerry | ............... | A61F 2/3868 623/20.31 |
| 2014/0330388 | A1* | 11/2014 | Mizuguchi | ........... | A61F 2/38 623/20.21 |

FOREIGN PATENT DOCUMENTS

| WO | WO 2013099661 A1 * | 7/2013 | ............ A61F 2/38 |
|---|---|---|---|
| WO | WO-2014150038 A1 | 9/2014 | |

OTHER PUBLICATIONS

"International Application Serial No. PCT/US2014/021955, Written Opinion mailed Jun. 2. 2014", 7 pgs.

Asano, T., et al., "In Vivo Three-Dimensional Patellar Tracking on the Femur", Clinical Orthopaedics and Related Research, No. 413, (Aug. 2003), pp. 222-232.

Barink, M., et al., "The Trochlea is Bilinear and Oriented Medially", Clinical Orthopaedics and Related Research, No. 411, (Jun. 2003), pp. 288-295.

Brick, G. W., et al., "The Patellofemoral Component of Total Knee Arthroplasty", Clinical Orthopaedics and Related Research, No. 231, (Jun. 1988), 163-178.

Chiu, Fang-Yao, "Native femoral sulcus as a guide for the position of the femoral component in primary total knee arthroplasty, A prospective comparative study of 420 knee", Knee Surg Sports Traumatol Arthrosc, vol. 14, (2006), 437-442.

Coughlin, K. M., et al., "Tibial Axis and Patellar Position Relative to the Femoral Epicondylar Axis During Squatting", The Journal of Arthroplasty, vol. 18 No. 8, (2003), 1048-1055.

Eckhoff, D. G., et al., "Locatin of the Femoral Sulcus in the Osteoarthritic Knee", The Journal of Arthroplasty, vol. 11 No. 2, (Feb. 1996), 163-165.

Eckhoff, D. G., et al., "Sulcus Morphology of the Distal Femur", Clinical Orthopaedics and Related Research, No. 331, (Oct. 1996), pp. 23-28.

Feinstein, W. K., et al., "Anatomic Alignment of the Patellar Groove", Clinical Orthopaedics and Related Research, No. 331, (Oct. 1996), pp. 64-73.

Hofmann, A. A., et al., "Patellar Component Medialization in Total Knee Arthroplasty", The Journal of Arthroplasty, vol. 12, No. 2, (Feb. 1997), 155-160.

Laprade, J., et al., "Real-time measurement of patellofemoral kinematics in asymptomatic subjects", The Knee, 12, (2005), 63-72.

Lewonowski, K., et al., "Medialization of the Patella in Total Knee Arthroplasty", The Journal of Arthtoplasty, vol. 12 No. 2, (Feb. 1997), 161-167.

Meijerink, H. J., et al., "The trochlea is medialized by total knee arthroplasty, An intraoperative assessment in 61 patients", Acta Orthopaedica, 78 (1), (2007), 123-127.

Nagamine, R., et al., "Patellar Tracking Measurement in the Normal Knee", Journal of Orthopaedic Research, vol. 13, No. 1, (1995), 115-122.

Nha, K. W., et al., "In Vivo Patellar Tracking: Clinical Motions and Patellofemoral Indices", Journal of Orthopaedic Research, (Aug. 2008), 1067-1074.

Rhoads, D. D., et al., "The Effect of Femoral Component Position on Patellar Tracking After Total Knee Arthroplasty", Clinical Orthopaedics and Related Research, No. 260, (Nov. 1990), 43-51.

Van Kampen, A., et al., "The Three-Dimensional Tracking Pattern of the Human Patella", Journal of Orthopaedic Research, vol. 8, No. 3, (1990), 372-382.

Yoshii, I., et al., "The Effect of Patellar BUtton Placement and Femoral Component Design on Patellar Tracking in Total Knee Arthroplasty", Clinical Orthopaedics and Related Research, No. 275, (Feb. 1992), 211-219.

"Application Serial No. PC17US2014/021955, International Preliminary Report on Patentability mailed Sep. 24, 2015", 9 pgs.

\* cited by examiner

PROSTHETIC KNEE IMPLANT

CLAIM OF PRIORITY

This application claims the benefit of U.S. Provisional Patent Application Ser. No. 61/784,521, filed on Mar. 14, 2013, the benefit of priority of which is claimed hereby, and which is incorporated by reference herein in its entirety.

BACKGROUND

Orthopedic prostheses are commonly utilized to prepare and/or replace damaged bone and tissue in the human body. For example, a prosthetic knee implant can be used to restore natural knee function by repairing damaged or diseased articular surfaces of a femur, a tibia, or both. Knee implants can include a femoral component implanted on the distal end of a femur, which articulates with a natural tibia or with a tibial component implanted on the corresponding proximal end of tibia. The femoral and tibial components can cooperate to restore the function of healthy natural knee.

OVERVIEW

This present disclosure is directed to knee implants and methods for implanting the knee implants. Using the knee implants and methods, a surgeon can achieve improved or optimal patella tracking while avoiding overhang of the femoral component.

The present inventors have recognized, among other things, that existing implants and methods can fail to provide a knee prosthesis with optimal patella tracking while minimizing or eliminating overhang of the femoral component relative to adjacent bone (e.g., the femur). A surgeon using an existing implant and method can shift a femoral component laterally, relative to what the instructions for use suggest, to attempt to allow a patella to track more laterally in flexion. However, a surgeon can be limited in how far the femoral component can be shifted laterally before the femoral component begins to overhang the femur. Therefore, in some instances the surgeon compromises between optimal patella tracking and avoiding overhang. The overhang can occur over the lateral periphery of the femoral bone or over the medial edge of the intercondylar notch and can be problematic for knee joint soft tissue.

The implants and methods of the present disclosure can provide or use a prosthetic knee implant comprising a femoral component. The femoral component can include a medial condyle and a lateral condyle, each of the condyles defining respective distal-most points and having substantially equal widths, as measured from a condyle medial side to a condyle lateral side and proximate the distal portion. The width of each of the condyles can define respective condyle midpoints located halfway between the condyle medial sides and the condyle lateral sides, where the distal-most points can be located laterally from the midpoints. The femoral component can further include a trochlear groove defining a distal-most sulcus point located halfway between the distal-most point of the medial condyle and the distal-most point of the lateral condyle.

The distal-most sulcus point of the trochlear groove can be shifted laterally with respect to the midpoint located halfway between the medial condyle and the lateral condyle midpoints. The lateralized trochlear groove can facilitate lateralization of the patella before further adjusting the femoral component laterally. Even if a surgeon decides to further lateralize the femoral component, the amount the femoral component of the present disclosure is further lateralized, to provide optimal patellar tracking, can be reduced or minimized, as compared to a femoral component that has a centralized distal-most sulcus point of the trochlear groove.

Additionally, the widths of the medial and lateral condyle can be substantially equal. The equal widths of the medial and lateral condyles can allow the intercondylar notch to remain centered between the medial and lateral condyles, while providing a lateralized trochlear groove. Maintaining the centrality of the intercondylar notch can enable a surgeon to make an intercondylar box cut more central (e.g., less laterally) on the femur, as compared to a femoral component with a lateralized intercondylar notch. If the intercondylar box cut is shifted laterally, as with other approaches to knee implants, the risk of a fracture across the lateral condylar bridge of the femur can increase. Therefore, the knee implants and methods of the present disclosure can advantageously reduce patellar maltracking, reduce or minimize or eliminate overhang, and reduce the risk of fracture.

To better illustrate examples of the prosthesis knee implants and methods disclosed herein, a non-limiting list of examples is provided here:

In Example 1, a prosthetic knee implant comprises a femoral component having a femur-contacting surface, an opposing articulation surface, and proximal, distal, anterior and posterior portions. The femoral component can include a medial condyle and a lateral condyle, each of the condyles defining respective distal-most points and having substantially equal widths, as measured from a condyle medial side to a condyle lateral side and proximate the distal portion. The width of each of the condyles defining respective condyle midpoints halfway between the condyle medial sides and the condyle lateral sides, the distal-most points located laterally from the midpoints. The femoral component can include a trochlear groove, proximate the anterior portion, defining a distal-most sulcus point located halfway between the distal-most point of the medial condyle and the distal-most point of the lateral condyle.

In Example 2, the implant of Example 1 is optionally configured such that the distal-most point of the medial condyle is located laterally at a first distance from the medial condyle midpoint and the distal-most point of the lateral condyle is located laterally at a second distance, equal to the first distance, from the lateral condyle midpoint.

In Example 3, the implant of Examples 1 or 2 is optionally configured such that the first distance and the second distance are between 1.0 millimeter and 4.0 millimeters, inclusive.

In Example 4, the implant of any one or any combination of Examples 1-3 is optionally configured such that the trochlear groove defines a patellar axis, when viewed from an anterior side of the femoral component, oriented substantially perpendicular to a plane connecting the distal-most point of the medial condyle and the distal-most point of the lateral condyle.

In Example 5, the implant of any one or any combination of Examples 1-4 is optionally configured such that the trochlear groove defines a patellar axis, when viewed from an anterior side of the femoral component, oriented substantially perpendicular to a plane connecting the medial condyle midpoint and the lateral condyle midpoint.

In Example 6, the implant of any one or any combination of Examples 1-5 is optionally configured such that the width of each of the condyles is between 19 millimeters and 31 millimeters, inclusive.

In Example 7, the implant of any one or any combination of Examples 1-6 optionally further includes a box-like projection extending from the femur-contacting surface and located halfway between the medial condyle midpoint and the lateral condyle midpoint.

In Example 8, the implant of any one or any combination of Examples 1-7 optionally further includes a concave surface extending between the medial and lateral condyles, the concave surface defining a proximal-most point halfway between the medial condyle distal-most point and the lateral condyle distal-most midpoint.

In Example 9, the implant of any one or any combination of Examples 1-8 optionally further includes a tibial component having a tibial-contacting surface, an opposing articulation surface, and proximal and distal portions.

In Example 10, the implant of any one or any combination of Examples 1-9 is optionally configured such that the articulation surface includes a medial dished surface portion and a lateral dished surface portion, each of the dished surface portions defining respective distal-most points and widths, as measured from a surface portion medial side to a surface portion lateral side, the width of each of the dished surface portions defining respective dished surface portion midpoints halfway between the surface portion medial sides and the surface portion lateral sides, the distal-most points located laterally from the midpoints.

In Example 11, the implant of any one or any combination of Examples 1-10 is optionally configured such that the distal-most point of the medial dished surface portion is located laterally a third distance from the medial dished surface portion midpoint and the distal-most point of the lateral dished surface portion is located laterally a fourth distance, equal to the third distance, from the lateral dished surface portion midpoint.

In Example 12, the implant of any one or any combination of Examples 1-11 is optionally configured such that the first and second distances are equal to the third and fourth distances.

In Example 13, the implant of any one or any combination of Examples 1-12 is optionally configured such that the medial dished surface portion and the lateral dished surface portion are asymmetrical, when viewed from a posterior side of the tibial component.

In Example 14, the implant of any one or any combination of Examples 1-13 is optionally configured such that the medial dished surface portion and the lateral dished surface portion are symmetrical, when viewed from a posterior side of the tibial component.

In Example 15, the implant of any one or any combination of Examples 1-14 is optionally configured such that the tibial component further comprises a tibial post extending from the articulation surface and located halfway between the medial dished surface portion midpoint and the lateral dished surface portion midpoint.

In Example 16, the implant of any one or any combination of Examples 1-15 is optionally configured such that the articulation surface further comprises a convex ridge surface extending between the medial and lateral dished surface portions, the convex ridge surface defining a proximal-most point halfway between the medial dished surface portion midpoint and the lateral dished surface portion midpoint.

In Example 17, the implant of any one or any combination of Examples 1-16 is optionally configured such that the tibial component includes a plate component, including the tibial-contacting surface, and a bearing component, including the articulation surface.

In Example 18, a method comprises implanting a femoral component, of a prosthetic knee implant, having a femur-contacting surface and an opposing articulation surface onto a distal end of a resected femur, including establishing artificial medial and lateral condyles of equal width and having distal-most points located laterally from respective condyle midpoints, and further establishing an artificial trochlear groove defining a distal-most sulcus point located halfway between the distal-most points of the artificial medial condyle and the distal-most point of the lateral condyle. The method includes implanting a tibial component, of the prosthetic knee implant, having a tibial-contacting surface and an opposing articulation surface onto a proximal end of a resected tibia, including establishing artificial medial and lateral dished surface portions having distal-most points on the articulation surface located laterally from respective dished surface portion midpoints.

In Example 19, the method of Example 18 is optionally configured such that establishing artificial medial and lateral condyles having distal-most points located laterally from the respective condyle midpoints includes lateralizing the distal-most points between 1.0 millimeter and 4.0 millimeters, relative to the condyle midpoints.

In Example 20, the method of any one or any combination of Examples 18 or 21 is optionally configured such that establishing the artificial trochlear groove includes lateralizing the distal-most sulcus point between 1.0 millimeter and 4.0 millimeters, relative to a position halfway between the condyle midpoints.

In Example 21, the method of any one or any combination of Examples 18-20 is optionally configured such that establishing the artificial medial and lateral dished surface portions having distal-most points on the articulation surface located laterally from the respective dished surface portion midpoints includes lateralizing the distal-most points between 1.0 millimeter and 4.0 millimeters, relative to the dished surface portion midpoints.

In Example 22, the method of any one or any combination of Examples 18-21 is optionally configured such that implanting the femoral component further includes establishing a box-like projection extending from the femur-contacting surface and located halfway between the medial condyle midpoint and the lateral condyle midpoint.

In Example 23, the method of any one or any combination of Examples 18-22 is optionally configured such that implanting the tibial component further includes establishing a tibial post extending from the articulation surface and located halfway between the medial dished surface portion midpoint and the lateral dished surface portion midpoint.

In Example 24, the method of any one or any combination of Examples 18-23 is optionally configured such that implanting the tibial component includes implanting a tibial base plate, including the tibial-contacting surface, and a bearing component, including the articulation surface.

These and other examples and features of the present knee implant and methods will be set forth in part in the following Detailed Description. This Overview is intended to provide non-limiting examples of the present subject matter—it is not intended to provide an exclusive or exhaustive explanation. The Detailed Description below is included to provide further information about the present knee implant and methods.

BRIEF DESCRIPTION OF THE DRAWINGS

In the drawings, like numerals can be used to describe similar elements throughout the several views. Like numerals having different letter suffixes can be used to represent different views or features of similar elements. The drawings illustrate generally, by way of example, but not by way of limitation, various embodiments discussed in the present document.

DETAILED DESCRIPTION

Figure 1:
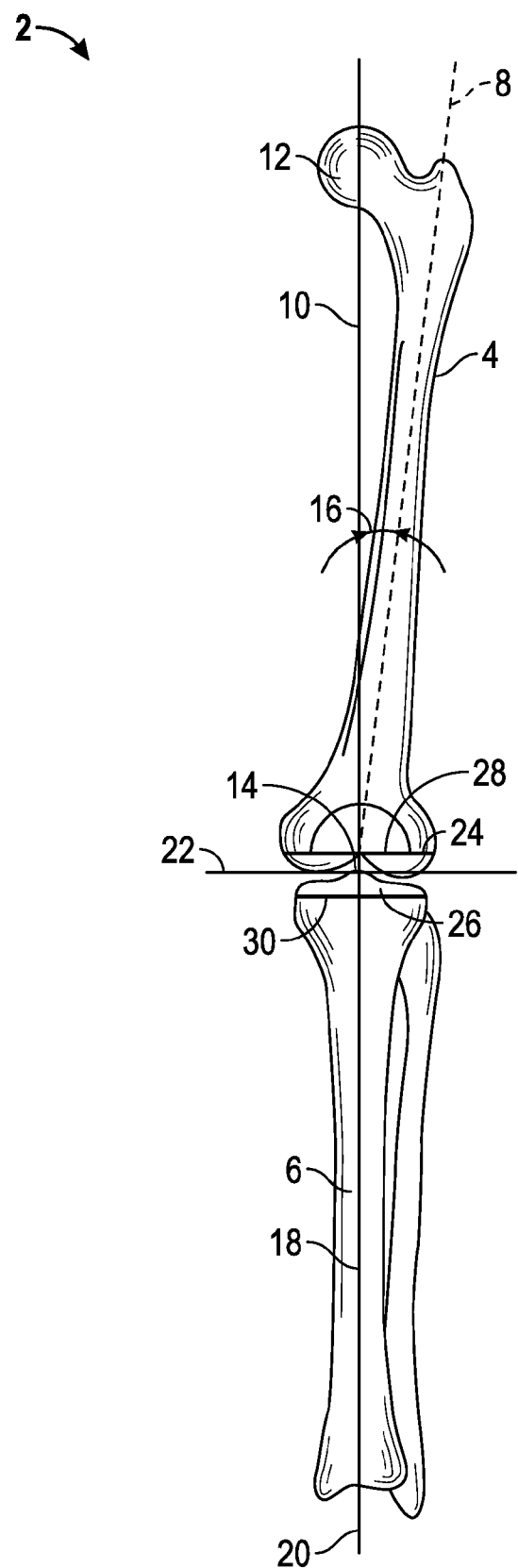
FIGS. 1-2 illustrate knee joint structures providing suitable environments in which a prosthetic knee implant can be used, in accordance with at least one example of the present disclosure.
Figure 2:
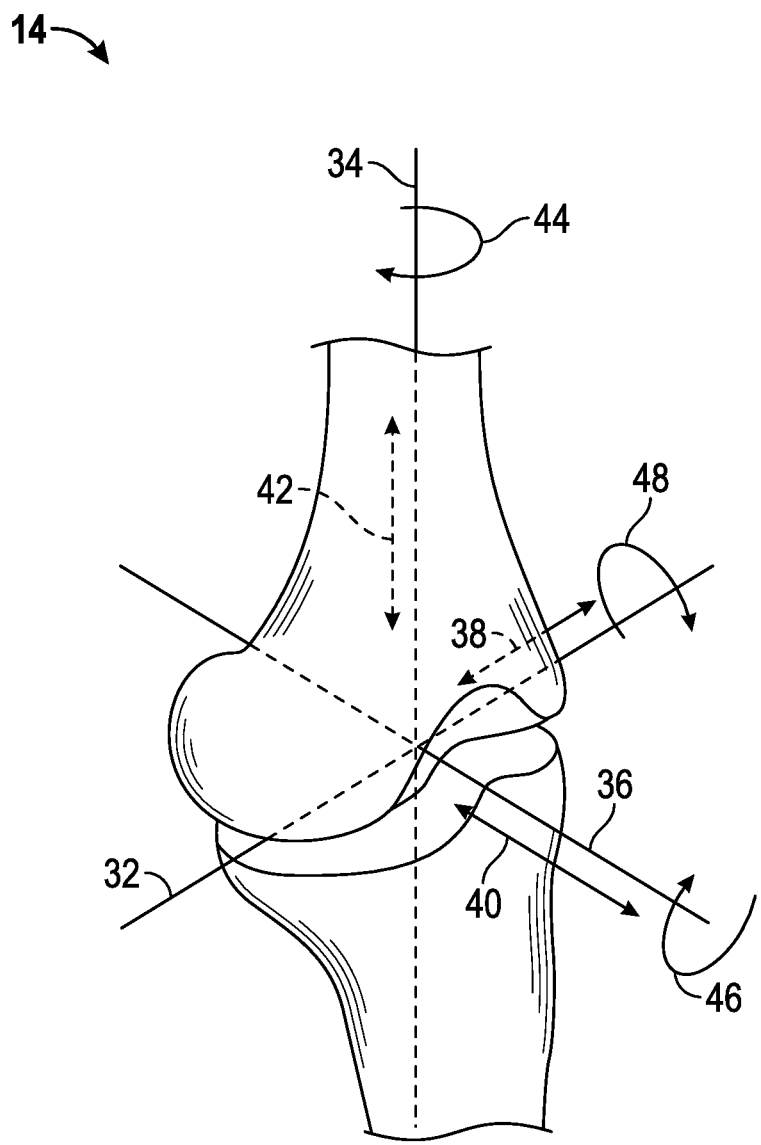

To better understand knee joint replacement procedures, it can be helpful to understand the relationship of bones and bone cuts that can be made to orient various provisional and permanent prosthesis components within a knee joint. FIGS. 1 and 2 illustrate several features of knee joint structures and orientations. In FIG. 1, a frontal view of a lower limb 2, including a femur 4 and a tibia 6, is shown to illustrate various lower limb axes. The femur 4 has a longitudinal anatomic axis 8 that coincides generally with its intramedullary canal. The femur 4 also has a generally longitudinal mechanical axis 10, or load axis, running from the center of a femoral head 12 to the center of a knee joint 14. The angle 16 extending between these two axes varies among the patient population, but is generally on the order of between 5-7 degrees, inclusive. Like the femur 4, the tibia 6 also has a longitudinal anatomic axis coinciding generally with its intramedullary canal. The generally longitudinal mechanical axis 18 of the tibia 6 runs from the center of the knee joint 14 to the center of an ankle region 20 and is generally collinear with its anatomic axis.

A joint line 22, about which the knee joint 14 flexes, is approximately parallel to a line through medial and lateral femoral condyles 24 and to a tibial plateau 26. Although illustrated as perpendicular in FIG. 1, the joint line 22 can extend at a varus or valgus angle relative to the mechanical axes 10 and 18 of the femur 4 and tibia 6, respectively. During a partial or total knee replacement procedure, portions of a distal end of the femur 4 or a proximal end of the tibia 6 can be resected to be parallel or approximately parallel to the joint line 22, and thus perpendicular to the mechanical axes 10 and 18, as indicated at 28 and 30, respectively.

FIG. 2 illustrates a closer view of the knee joint 14 and its coordinate system, in which a medial/lateral axis 32 corresponds approximately to the joint line 22 (illustrated in FIG. 1), a proximal/distal axis 34 corresponds approximately to the mechanical axes 10 and 18 (illustrated in FIG. 1), and an anterior/posterior axis 36 is approximately normal to the other two axes. Position along each of these axes can be depicted by arrows, which can represent the medial/lateral 38, anterior/posterior 40, and proximal/distal 42 positioning of inserted prosthesis components. Rotation about each of these axes can also be depicted by arrows. Rotation about the proximal/distal axis 34 can correspond anatomically to external rotation of a femoral component, while rotation about the anterior/posterior axis 36 and medial/lateral axis 32 can correspond to varus/valgus angle and extension plane slope of a component, respectively. Depending on a position of the proximal tibial cut 30 (illustrated in FIG. 1) made, a varus/valgus angle 46, extension plane angle 48, external rotation 50, or joint extension or flexion gap can be affected. Similarly, a position of the distal femoral cut 28 (illustrated in FIG. 1) can affect the location of the joint line 22, the extension gap, the varus/valgus angle 46, or the extension plane angle 48.

Figure 3:
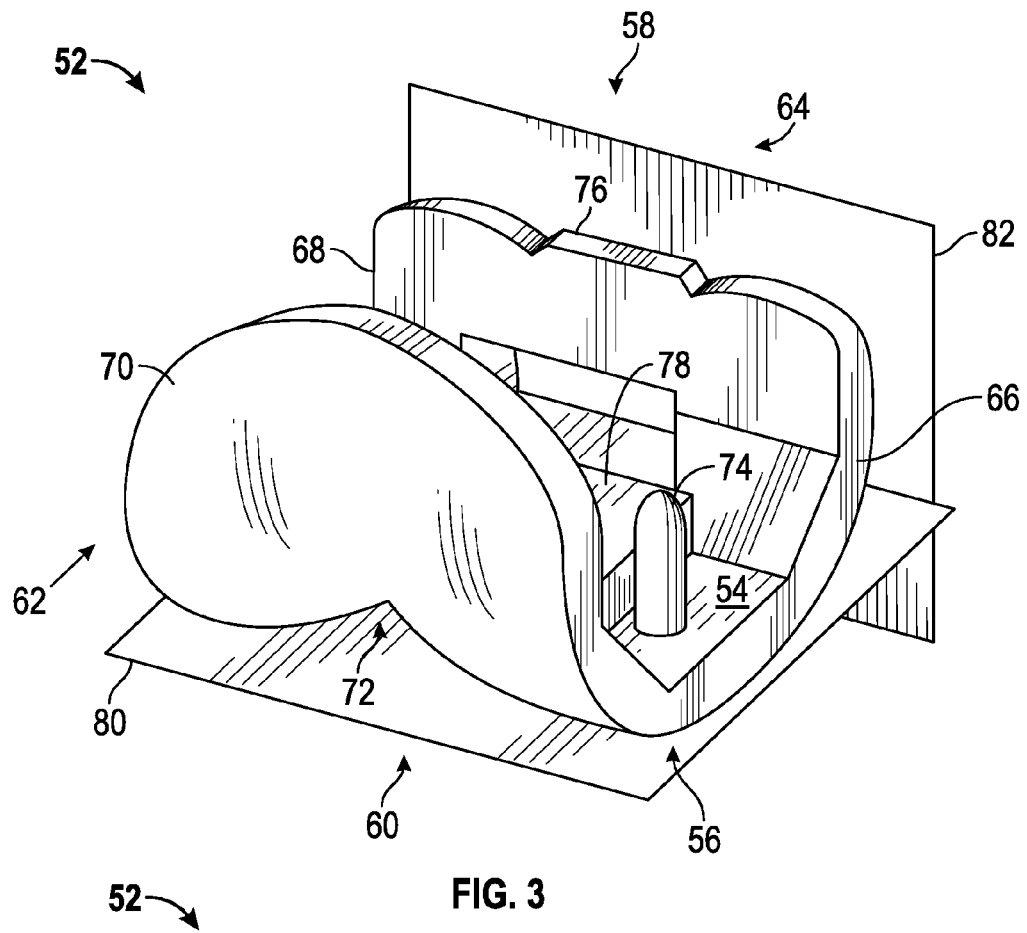
FIG. 3 illustrates a perspective view of a femoral component of a prosthetic knee implant, in accordance with at least one example of the present disclosure.

FIG. 3 illustrates a perspective view of a femoral component 52, in accordance with at least one example of the present disclosure. The femoral component 52 can include a femur-contacting surface 54 formed along the inner periphery of the femoral component 52. The femur-contacting surface 54 can be configured to contact a distal end of a femur. An opposing articulation surface 56 can be disposed opposite of the femur-contacting surface 54. The articulation surface 56 can include a lateral condyle 66 and a medial condyle 68. The lateral condyle 66 and the medial condyle 68 can be configured for articulation with a natural tibia or with a prosthetic tibial component. The femoral component 52 can include a proximal portion 58, a distal portion 60, an anterior portion 62, and a posterior portion 64.

The femoral component 52 can include an anterior flange 70. The anterior flange 70 can have a trochlear groove 72 that is proximate the anterior portion 60. The trochlear groove 72 can extend from a generally anterior and proximal starting point to a generally posterior and distal terminus. The trochlear groove 72 can form an anterior articular surface of the femoral component 52 for articulation with a natural or prosthetic patella. An example of a prosthetic patella that can be used with the femoral component 52 is described in U.S. Patent Publication 2012/0179264 A1, filed Dec. 6, 2011 (entitled "PROSTHETIC PATELLA"), the entire disclosure of which is hereby incorporated by reference herein.

In the example illustrated in FIG. 3, the femoral component 52 can include one or more of fixation pegs 74, a box-like projection 78, and a posterior cam 76 in accordance with a "posterior stabilizing" femoral component design. The one or more fixation pegs 74 and the box-like projection 78 can extend from the femur-contacting surface 54. The fixation pegs 74 can be configured to be located within the distal end of a femur. The box-like projection 78 can be located halfway between a lateral condyle midpoint 90 and a medial condyle midpoint 91 (illustrated in FIG. 5A). In an example, the femoral component 52 can include two fixation pegs 74, where each fixation peg 74 can be located adjacent or near a side of the box-like projection 78. For example, a first fixation peg 74 can be located laterally with respect to the box-like projection 78 and a second fixation peg can be located laterally with respect to the box-like projection 78.

The femoral component 52 can be modified for particular applications. For example, the posterior cam 76, the box-like projection 78, or both can be eliminated or modified for a particular application such as, for example, a "cruciate retaining" femoral component design that does not include at least one of the posterior cam 76 and the box-like projection 78.

Figure 4:
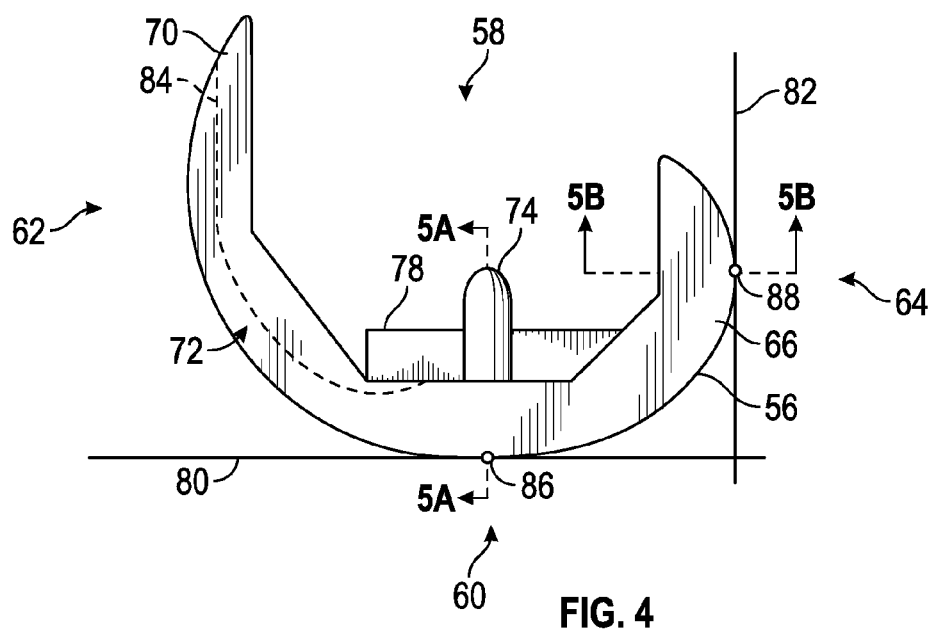
FIG. 4 illustrates a side view of the femoral component shown in FIG. 3, in accordance with at least one example of the present disclosure.

The femoral component 52 can define a transverse plane 80. The transverse plane 80 can be a plane tangent to distal-most points of the lateral and medial condyles 66, 68. The femoral component 52 can also define a coronal plane 82. The coronal plane 82 can be a plane tangent to the posterior-most points of the lateral and medial condyles 66, 68 and, when viewed from a lateral side of the femoral component 52, can be perpendicular to the transverse plane 80 (as illustrated in FIG. 4). When the femoral component 52 is flexed or rotated approximately 90 degrees about the medial/lateral axis 32 (as illustrated in FIG. 2), the posterior-most points can be positioned at the locations shown for the distal-most points and contact the transverse plane 80.

Figure 7A:
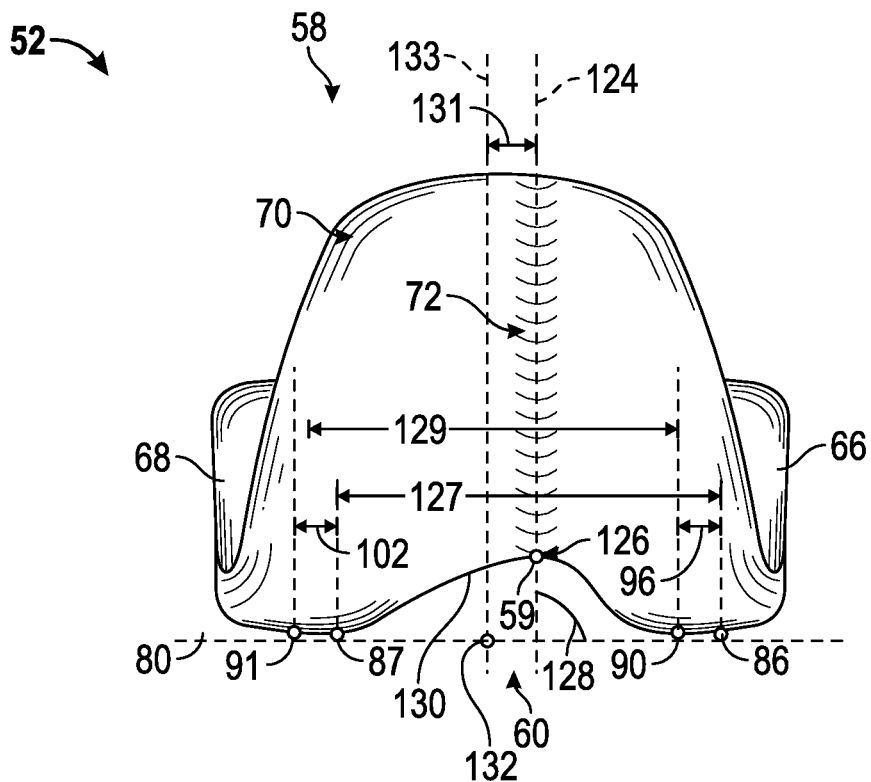
FIG. 7A illustrates a front view of a femoral component, in accordance with at least one example of the present disclosure.
Figure 7B:
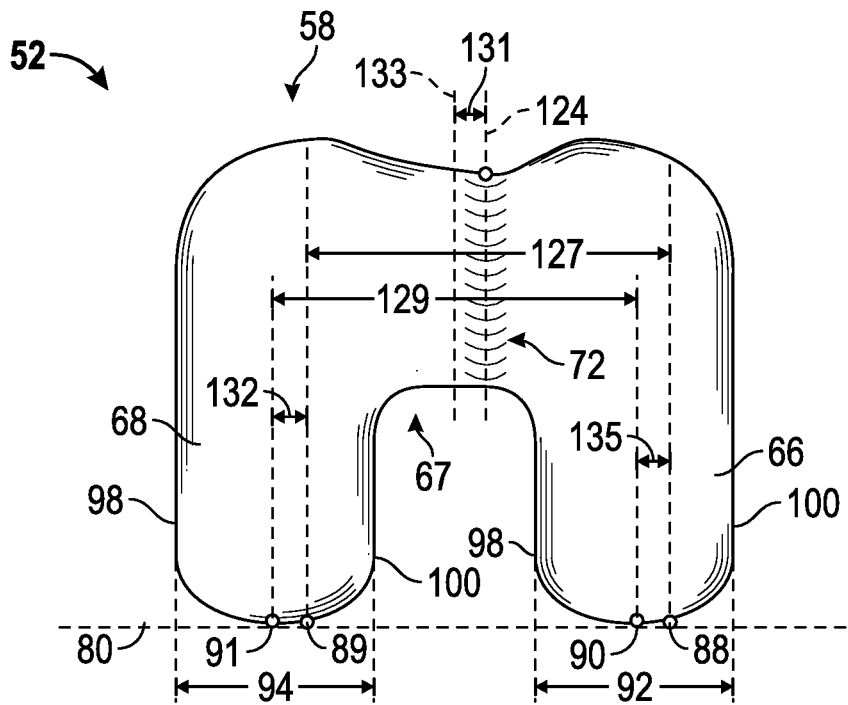
FIG. 7B illustrates a front view of the femoral component of FIG. 7A when the femoral component is rotated approximately 90 degrees about a medial/lateral axis, in accordance with at least one example of the present disclosure.

FIG. 4 illustrates a side view of the femoral component 52 shown in FIG. 1, in accordance with at least one example of the present disclosure. The femoral component 52 can include a trochlear groove 72 that can define a patellar axis 124 (as shown in FIGS. 7A & 7B) and a trochlear curve 84. The patellar axis 124 and the trochlear curve 84 can be projections of a "valley line" formed along the deepest part of the valley-like concavity formed by the trochlear groove 72. The deepest part of the valley can be referred to as the sulcus of the trochlear groove.

As illustrated in the example of FIG. 4, the lateral condyle 66 can include a distal-most point 86 and a posterior-most point 88. The distal-most point 86 can contact the transverse plane 80 and the posterior-most point 88 can contact the coronal plane 82. As described herein, when the femoral component 52 is flexed or rotated approximately 90 degrees about the medial/lateral axis 32, the posterior-most point 88 can be positioned at the locations shown for the distal-most point of the femoral component 52 and can contact the transverse plan 80. Respective distal-most ridges can extend along each of the lateral and medial condyles 66, 68 between the distal-most points and the posterior most-points. As the femoral component 52 is flexed or rotated a distal-most point of the lateral and medial condyles 66, 68 contacts the transverse plane 80. The distal-most ridge can extend from the distal-most points of the lateral and medial condyles to the posterior-most points of the lateral and medial condyles.

Figure 5A:
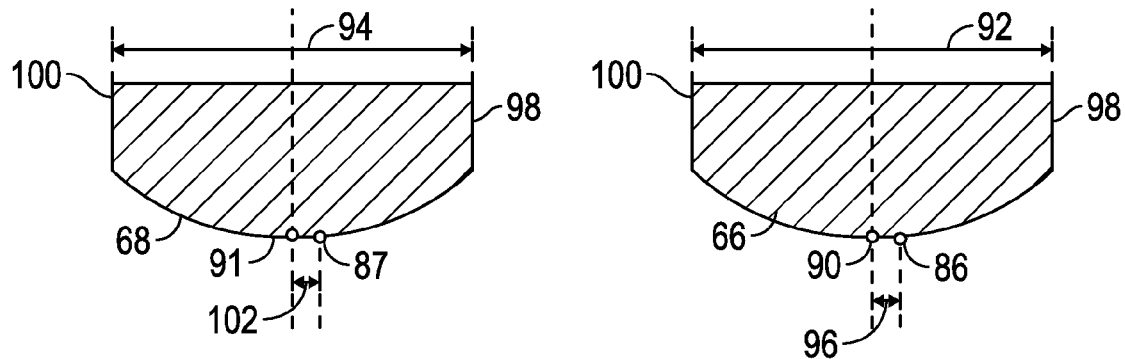
FIG. 5A illustrates a cross-sectional view of the femoral component in FIG. 4, along line A-A.

FIG. 5A illustrates a cross-sectional view of the femoral component 52 in FIG. 4, along line 5A-5A. As illustrated in the example of FIG. 5A, the lateral condyle 66 can define a lateral condyle distal-most point 86 and the medial condyle 68 can define a medial condyle distal-most point 87. The lateral condyle 66 can have a width 92 and the lateral condyle 68 can have a width 94. In an example, the width 92 of the lateral condyle 66 can be substantially equal to the width 94 of the lateral condyle 68. In an example, the lateral and medial condyles 66, 68 of the femoral component 52 can include two vertical surfaces, an innermost and outermost surface, that can define a condyle width. For example, the widths 92, 94 of the lateral and medial condyles 66, 68 can be measured from a condyle lateral side 98 to a condyle lateral side 100. In an example, the widths 92, 94 of the lateral and medial condyles 66, 68 can be within a range of from about 19 millimeters to about 31 millimeters, inclusive. Other widths of the lateral and medial condyles 66, 68 can be used and can be based on one or more factors, such as for example, the specific anatomy of a patient.

The widths 92, 94 of the lateral and medial condyles 66, 68 can define respective condyle midpoints. For example, the lateral condyle 66 can define a lateral condyle midpoint 90 and the medial condyle 68 can define a medial condyle midpoint 91. The lateral and medial condyle midpoints 90, 91 can be located halfway between the condyle lateral side 98 and the condyle medial side 100 of the lateral and medial condyles 66, 68. The distal-most points 86, 87 can be located laterally from the midpoints 90, 91, respectively. For example, the lateral condyle distal-most point 86 can be located laterally at a distance 96 from the lateral condyle midpoint 90 and the medial condyle distal-most point 87 can be located laterally at a distance 102 from the medial condyle midpoint 91. The distance 96 can be substantially equal to the distance 102. In an example, the distances 96 and 102 can be within a range of from about 1.0 millimeter to 4.0 millimeters, inclusive. Other distances can be used and can be based on one or more factors, such as for example, the specific anatomy of a patient.

Figure 5B:
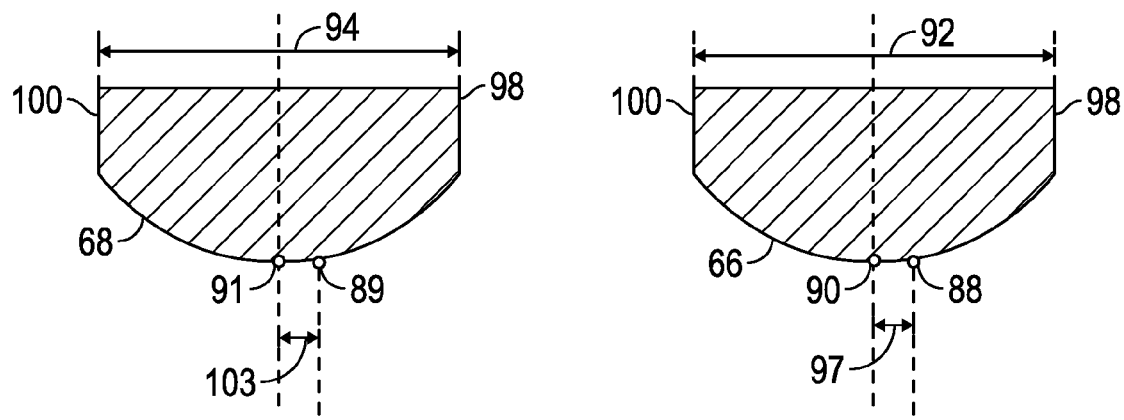
FIG. 5B illustrates a cross-sectional view of the femoral component in FIG. 4, along line B-B.

FIG. 5B illustrates a cross-sectional view of the femoral component in FIG. 4, along line 5B-5B. The cross-sectional view illustrated in FIG. 5B can be substantially identical to the cross-sectional view in FIG. 5A. In FIG. 5B, the lateral condyle 66 and the medial condyle 68 define respective posterior-most points 88, 89. For example, the lateral condyle 66 can define a lateral condyle posterior-most point 88 and the medial condyle 68 can define a medial condyle posterior-most point 89. The lateral and medial condyle 66, 68 can have substantially equal widths 92, 94, as measured from a condyle lateral side 98 to a condyle lateral side 100. As described herein, the widths 92, 94 of the lateral and medial condyles 66, 68 can define respective condyle midpoints 90, 91. The lateral and medial condyle midpoints 90, 91 can be located halfway between the condyle lateral side 98 and the condyle medial side 100 of the lateral and medial condyles 66, 68, respectively.

The posterior-most points 88, 89 can be located laterally from the midpoints 90, 91, respectively. For example, the lateral condyle posterior-most point 88 can be located laterally at a distance 97 from the lateral condyle midpoint 90 and the medial condyle posterior-most point 89 can be located laterally at a distance 103 from the medial condyle midpoint 91. In an example, the distances 97 and 103 can be substantially the same. Additionally, the distances 97 and 103 can be substantially the same as the distances 96 and 102 (as illustrated in FIG. 5A).

As described herein, the posterior-most points 88, 89 can be the points of the femoral component 52 that contact the coronal plane 82 (as illustrated in FIGS. 3 & 4). The distal-most ridge can extend along the lateral condyle 66 and the medial condyle 68. For example, the distal-most ridge of the lateral and medial condyles 66, 68 can extend from the lateral and medial condyle distal-most points 86, 87 to the lateral and medial condyle posterior-most point 88, 89. The distal-most points 86, 87 and the posterior-most points 88, 89 can be located laterally a same distance from the lateral and medial condyle midpoints 90, 91. Thus, when the femoral component 52 is flexed or rotated approximately 90 degrees about the medial/lateral axis 32, the points along the distal-most ridge can contact transverse plane 80 while the femoral component 52 is flexed or rotated.

As illustrated in FIGS. 5A and 5B, the lateral and medial condyles 66, 68 can be curved. However, the lateral and medial condyles 66, 68 can include other geometries. For example, the lateral and medial condyles 66, 68 can be curved, substantially flat, or a combination thereof.

Figure 6:
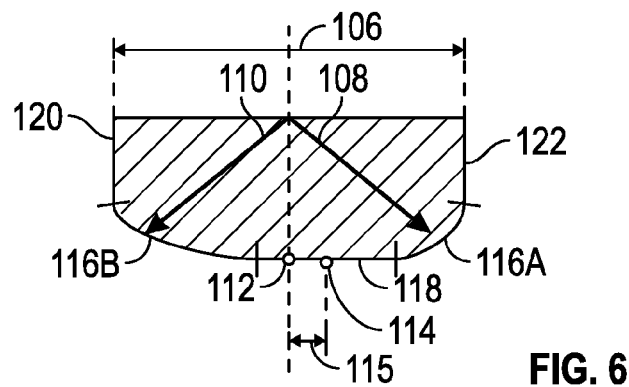
FIG. 6 illustrates a cross-sectional view of a condyle, in accordance with at least one example of the present disclosure.

FIG. 6 illustrates a cross-sectional view of a condyle 104, in accordance with at least one example of the present disclosure. The condyle 104, as illustrated in the example of FIG. 6, can include a combination of curved and flat surfaces. The condyle 104 can include curved surfaces 116A and 116B (collectively referred to as "curved surfaces 116") and a substantially flat surface 118 located between the two curved surfaces 116. A width 106 of the condyle 104 can be measured from a condyle medial side 120 to a condyle lateral side 122 and the midpoint 112 of the condyle 104 can be halfway between the condyle medial side 120 and the condyle lateral side 122.

The curved surfaces 116 can each include a different radius of curvature. For example, curved surface 116A can include a radius of curvature 108 and curved surface 116B can include a radius of curvature 110. In an example, the radius of curvature 108 can be different from the radius of curvature 110. For example, the radius of curvature 110 can be greater than the radius of curvature 108.

The substantially flat surface 118 can be located between the curved surfaces 116 and can have a distal-most point 114. The distal-most point 114 of the substantially flat surface 118 can be defined as the mid-point of the flat surface 118. As illustrated in the example of FIG. 6, the distal-most point 114 can be located at the center of the substantially flat surface 118. The distal-most point 144 can be located laterally from the midpoint 112. For example, the distal-most point 114 can be located a distance 115 from the midpoint 112. In an example, the distance 115 can be within a range of from about 1.0 millimeter to 4.0 millimeters, inclusive.

FIG. 7A illustrates a front view of a femoral component 52, in accordance with at least one example of the present disclosure. The femoral component 52 can include the trochlear groove 72. The trochlear groove 72 can define a distal-most sulcus point 126 that can be located halfway between the distal-most points 86, 87 of the lateral and medial condyles 66, 68. As discussed herein, the deepest part of the valley-like concavity formed by the trochlear groove 72 can be referred to as the sulcus of the trochlear groove 72.

The femoral component 52 can include a concave surface 130 extending between the lateral and medial condyles 66, 68. The concave surface 130 can define a proximal-most point 59 that can be located halfway between the lateral condyle distal-most point 86 and the medial condyle distal-most point 87 and substantially corresponds to the distal-most sulcus point 126. As illustrated in the example of FIG. 7A, the distal-most sulcus point 126 can be located halfway between the distal-most points 86, 87 of the lateral and medial condyles 66, 68. The distal-most sulcus point 126 can also be located laterally from an axis 133 extending from a midpoint 132 located between the lateral and medial condyle midpoints 90, 91. The distal-most sulcus point 126 can be shifted laterally a distance 131 from the axis 133 that can be substantially equal to the distances 96, 102 that the lateral and medial distal-most points 86, 87 are shifted laterally from the lateral and medial condyle midpoints 90, 91.

The trochlear groove 72 can also define a patellar axis 124. The patellar axis 124, when viewed from an anterior side of the femoral component 52, can form an angle 128 with respect to the transverse plane 80 that contacts the distal-most points 86, 87 of the lateral and medial condyles 66, 68. In an example, the patellar axis 124 can be oriented substantially perpendicular to the transverse plane 80 (e.g., within +/− four degrees, inclusive). That is, the angle 128 formed between the patellar axis 124 and the transverse plane 80 can be approximately 90 degrees. The patellar axis 124, when viewed from an anterior side of the femoral component 52, can also be oriented substantially perpendicular to a plane connecting the lateral and medial midpoints 90, 91.

In an example, the patellar axis 124, when viewed from an anterior side of the femoral component 52, can extend in a laterally diverging direction from the distal-most sulcus point 126 toward the proximal portion 58. In an example, the angle 128 formed between the transverse plane 80 and the patellar axis 124 can be an oblique angle (e.g., greater or less than 90 degrees).

In an example, a distance 129 between the lateral and medial condyle midpoints 90, 91 can be substantially equal to a distance 127 between the lateral and medial condyle distal-most points 86, 87. Thus, the distances 96, 102 that the lateral and medial condyle distal-most points 86, 87 are shifted from the lateral and medial condyle mid-points 90, 91 can be substantially the same.

FIG. 7B illustrates a front view of the femoral component 52 of FIG. 7A when the femoral component 52 is rotated approximately 90 degrees about a medial/lateral axis, in accordance with at least one example of the present disclosure. As illustrated in the example of FIG. 7B, the posterior-most points 88, 89 of the lateral and medial condyles 66, 68, when viewed from an anterior side of the femoral component 52, can contact with the transverse plane 80.

In an example, a distance 129 between the lateral and medial condyle midpoints 90, 91 can be substantially equal to a distance 127 between the lateral and medial condyle posterior-most points 88, 89. Again, the posterior-most points 88, 89 can be positioned at the locations shown for the distal-most points when the femoral component 52 is rotated or flexed approximately 90 degrees about the medial/lateral axis 32. Thus, the distances 96, 102 that the lateral and medial condyle distal-most points 86, 87 are shifted laterally from the lateral and medial condyle midpoints 90, 91 can be substantially the same.

The (1) widths 92, 94 of the lateral and medial condyles 66, 68, the (2) distances 90, 102 the distal-most points 86, 87 are shifted laterally from the midpoints 90, 91, and the (3) distance 131 (as illustrated in FIG. 7B) that the trochlear groove is shifted laterally from the axis 133 can vary, such as to account for natural variation among femurs of different patients. For example, such variations may arise from different bone sizes and geometries, and correspondingly different nature knee articulation characteristics, among patients of different gender, size, age, ethnicity, build, among other factors.

The lateral and medial condyles 66, 68 can define an intercondylar notch 67, which is the space between the lateral and medial condyles 66, 68. As illustrated in the example of FIG. 7B, the intercondylar notch 67 can be centered between the lateraland medial condyles 66, 68 having equal widths 92, 94. As described herein, having the intercondylar notch 67 located centrally between the lateral and medial condyles 66, 68 can enable a surgeon to make an intercondylar box cut substantially in the middle of the patient's femur, and thereby reduce the risk of fracture in a posterior-stabilized (PS) knee compared to a PS femoral component with a lateralized intercondylar notch.

Figure 8:
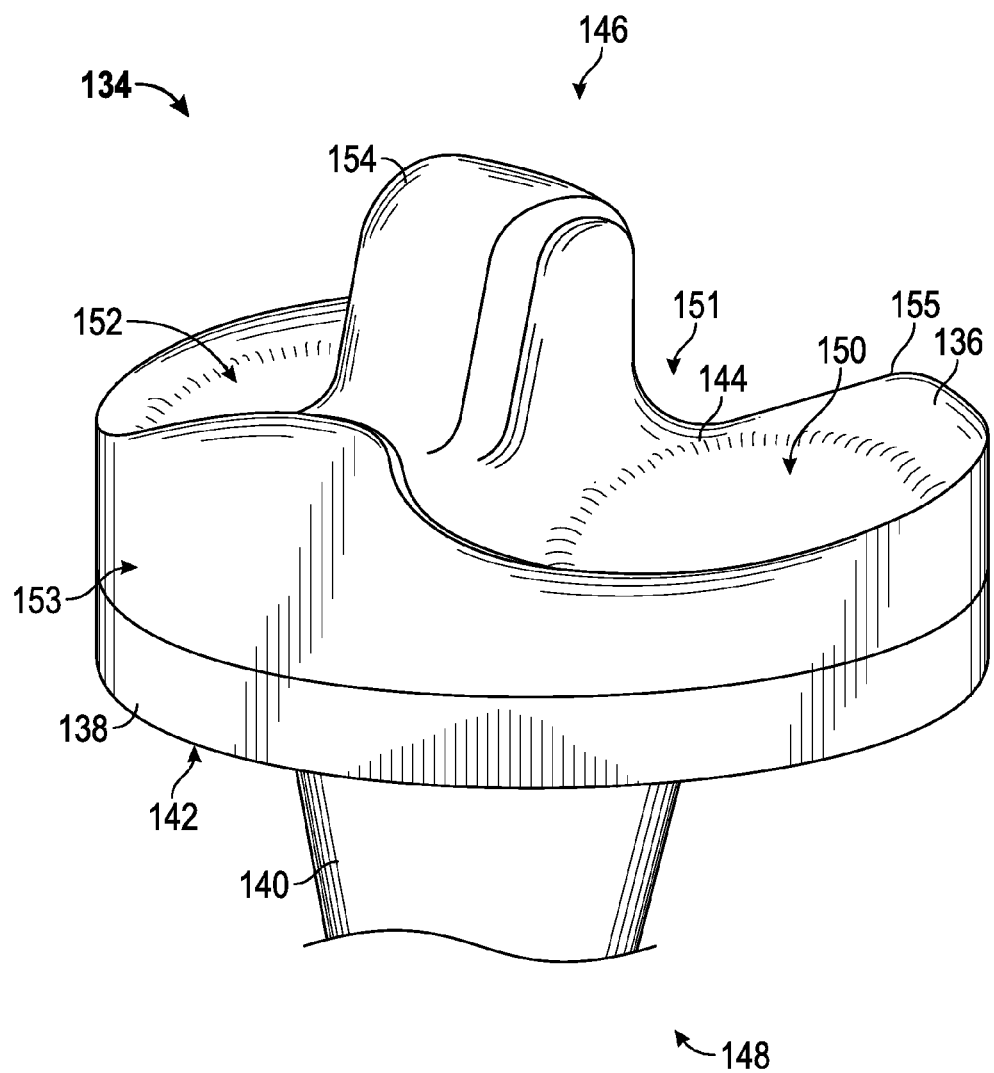
FIG. 8 illustrates a perspective view of a tibial component of a prosthetic knee implant, in accordance with at least one example of the present disclosure.

FIG. 8 illustrates a perspective view of a tibial component 134 of a prosthetic knee implant, in accordance with at least one example of the present disclosure. The tibial component 34 can be used alone or in conjunction with the femoral component 52 to provide a prosthetic knee implant. The tibial component 134 of FIG. 8 illustrates a bearing component 136 and a plate component 138. A stem component 140 can be attached or integral to the plate component 138 and can be used to secure the plate component 138 to a resected tibia. The plate component 138 can include a tibial-contacting surface 142 to contact the resected tibia and an opposing superior surface to interact with the bearing component 136.

The bearing component 136 can include an articulation surface 144, to articulate with natural or prosthetic condyles of a distal femur, and an opposing inferior surface, to interact with the superior surface of the plate component 138. The tibial component 134 can include a proximal portion 146, a distal portion 148, a proximate portion 151, and an anterior portion 153.

Figure 10:
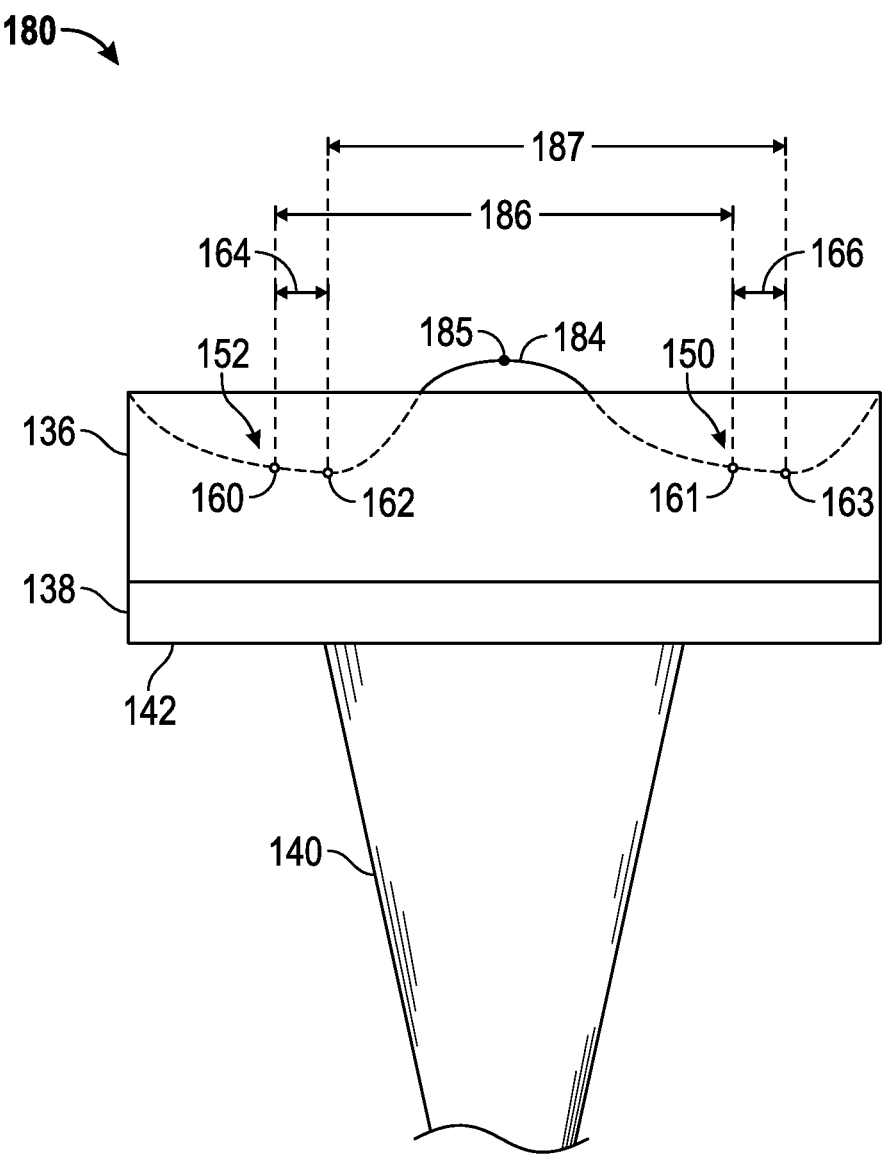
FIG. 10 illustrates a front view of a tibial component of a prosthetic knee implant, in accordance with at least one example of the present disclosure.

The articulation surface 144 can include a lateral dished surface portion 150 and a medial dished surface portion 152, with a central tibial eminence located between the lateral and medial dished surface portions 150, 152. As illustrated in the example of FIG. 8, the eminence can, for example, be a tibial post 154 in accordance with a "Posterior Stabilized" tibial component design. While the example illustrated in FIG. 8 represents an example of a "Posterior Stabilized" bearing component, it is contemplated that other tibial bearing components can be used, for example, "Cruciate Retaining" bearing components (such as illustrated in FIG. 10).

A posterior cruciate ligament (PCL) cutout 151 can be located at a posterior side 155 between the lateral and medial dished surface portions 150, 152. The PCL cutout 151 can be sized and located to correspond with a PCL of a knee joint. The bearing component 136 can be made available in a variety of shapes and sizes such as to accommodate a variety of patient knee joints.

The bearing component 136 can be located atop of the plate component 138 and the superior surface of the plate component 138 can contact the inferior surface of the bearing component 136. The bearing component 136 and the plate component 138 can be coupled to or engaged with each other. The plate component 138 can be coupled to the bearing component 136 by any of a variety of methods. In an example, either the superior surface of the plate component 138 or the inferior surface of the bearing component 136 can include one or more projections that can be received by a corresponding cavity in the corresponding superior surface of the plate component 138 or the inferior surface of the bearing component 136. Other coupling mechanisms are possible.

Figure 9:
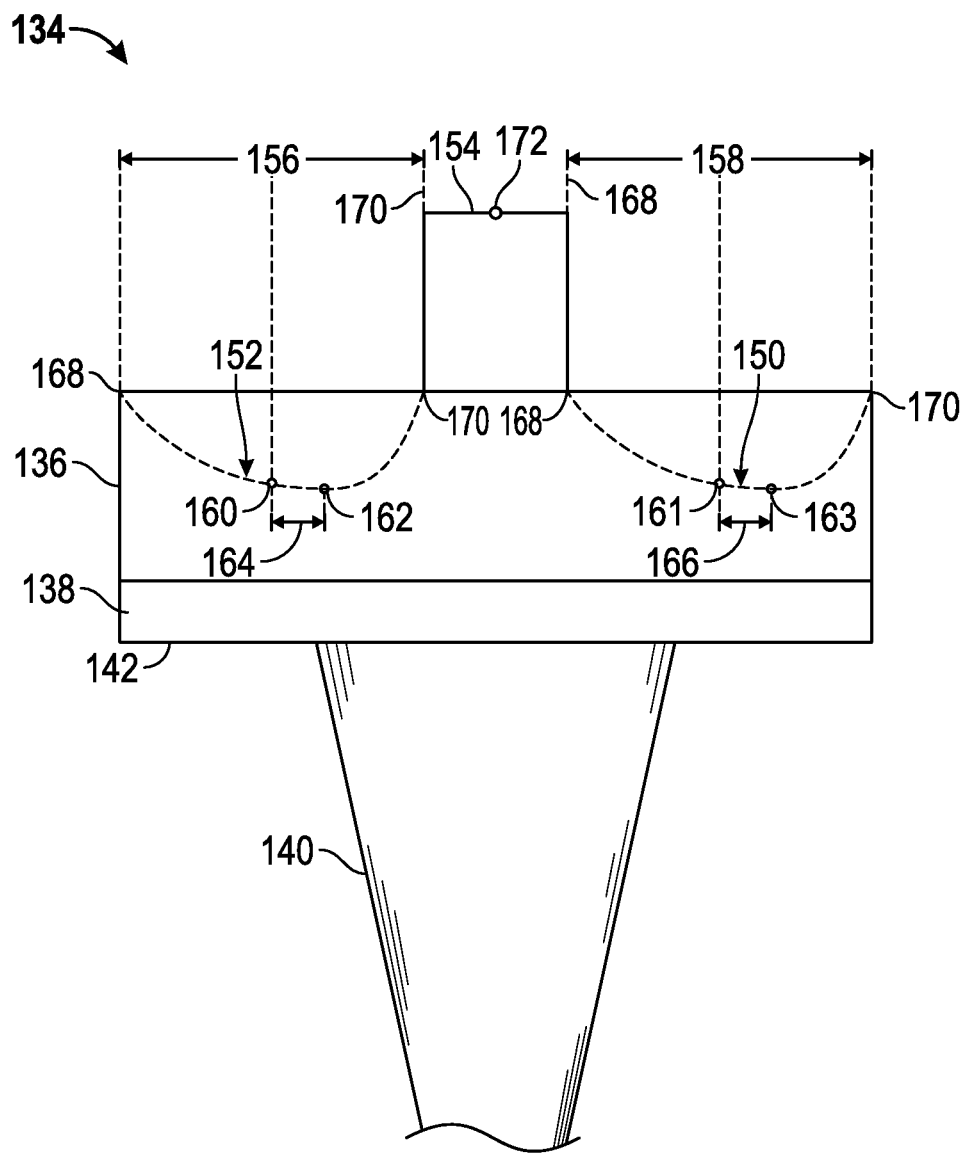
FIG. 9 illustrates a front view of a tibial component of a prosthetic knee implant, in accordance with at least one example of the present disclosure.

FIG. 9 illustrates a front view of a tibial component 134 of a prosthetic knee implant, in accordance with at least one example of the present disclosure. The lateral dished surface portion 150 can define a lateral dished surface distal-most point 163 and the medial dished surface portion 152 can define a medial dished surface distal-most point 162. The lateral dished surface portion 150 can have a width 158 and the medial dished surface portion 152 can have a width 156. In an example, the width 158 of the lateral dished surface portion 150 can be substantially equal to the width 156 of the medial dished surface portion 152. In an example, the lateral and medial dished surface portions 150, 152 can include innermost and outermost surfaces that can define a dished surface portion width. For example, the widths 156, 158 of the medial and lateral dished surface portions 152, 150 can be measured from a dished surface lateral side 170 to a dished surface medial side 168. In an example, the widths 156, 158 can also be measured by measuring a midpoint located halfway between a lateral edge of the bearing component 136 and a center point of the bearing component 136, where the center point is halfway between the medial edge and the lateral edge of the bearing component 136.

The widths 158, 156 of the lateral and medial dished surface portions 150, 152 can define respective dished surface midpoints. For example, the lateral dished surface portion 150 can define a lateral dished surface portion midpoint 161 and the medial dished surface portion 152 can define a medial dished surface portion midpoint 160. The lateral and medial dished surface portion midpoints 161, 160 can be located halfway between dished surface lateral sides 170 and the dished surface medial sides 168 of the lateral and medial dished surface portions 150, 152.

The lateral and medial dished surface portion distal-most points 163, 162 can be located laterally from the lateral and medial dished surface portion midpoints 161, 160, respectively. For example, the lateral dished surface portion distal-most point 163 can be located laterally at a distance 166 from the lateral dished surface portion midpoint 161 and the medial dished surface distal-most point 162 can be located laterally at a distance 164 from the medial dished surface portion midpoint 91. The distance 166 can be substantially equal to the distance 164. In an example, the distances 166 and 164 can be substantially equal to the distances 96, 103, and 131 (as illustrated in FIG. 7A), which can be within a range of from about 1.0 millimeter to 4.0 millimeters, inclusive. Other distances can be used and can be based on various factors, such as for example, the specific anatomy of the patient.

As illustrated in the example of FIG. 9, the tibial component 134 can include a tibial post 154 extending from the articulation surface 144 of the bearing component 136. The tibial post 154 can be located halfway between the lateral dished surface portion midpoint 161 and the medial dished surface portion midpoint 160. For example, a midpoint 172 of the tibial post 154 can be located halfway between the lateral dished surface portion midpoint 161 and the medial dished surface portion midpoint 160.

FIG. 10 illustrates a front view a tibial component 180 of a prosthetic knee implant, in accordance with at least one example of the present disclosure. The tibial component 180 illustrated in the example of FIG. 10 can be substantially similar to the tibial component 134 illustrated in FIG. 9; however, tibial component 180 need not include a tibial post. The tibial component 180 illustrated in FIG. 10 can include a convex ridge surface 184 extending between the lateral and medial dished surface portions 150, 152. For example, the tibial component 180 in FIG. 10 can be in accordance with a "Cruciate Retaining" tibial component design. The convex ridge surface 184 can define a proximal-most point 185 that is located halfway between the lateral dished surface portion midpoint 161 and the medial dished surface portion midpoint 160.

In an example, a distance 186 between the lateral and medial dished surface portion midpoints 161, 160 can be substantially equal to a distance 187 between the lateral and medial dished surface portion distal-most points 163, 162. Thus, the distance 166 that the lateral and medial dished surface portion distal-most points 163, 162 are shifted laterally from the lateral and medial dished surface portion midpoints 161, 160 are substantially the same.

The lateral dished surface portion 150 and the medial dished surface portion 152 can be symmetrical, when viewed from a posterior side of the tibial component. In an example, the lateral dished surface portion 150 and the medial dished surface portion 152 can be asymmetrical, when viewed from a posterior side of the tibial component. For example, while the dished surfaces 150, 152 are illustrated in FIG. 8 as having a circular shape, other geometries and configurations are possible.

Figure 11:
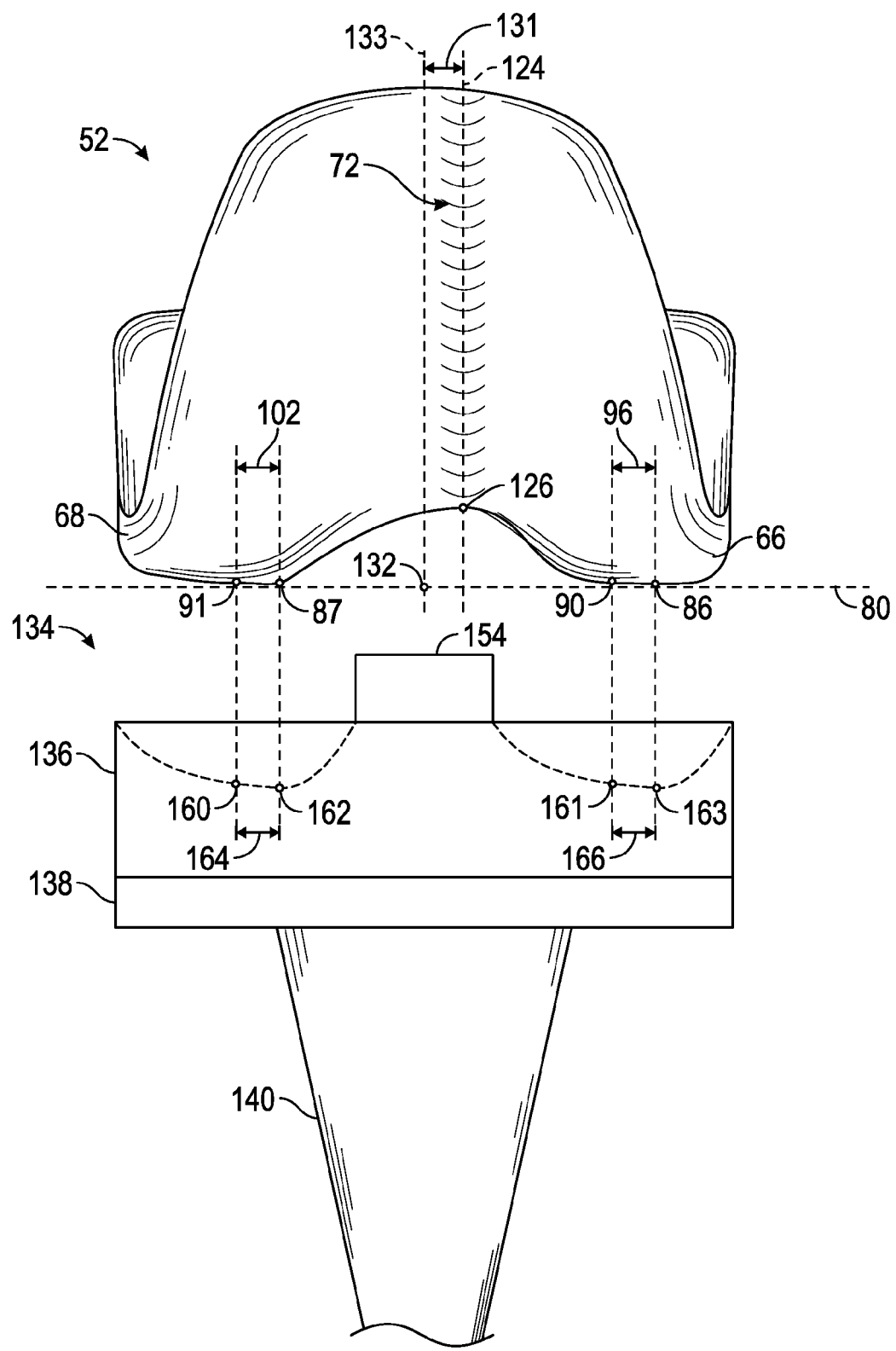
FIG. 11 illustrates a front view a femoral component and a tibial component of a prosthetic knee implant, in accordance with at least one example of the present disclosure.

FIG. 11 illustrates a front view a femoral component 52 and a tibial component 134 of a prosthetic knee implant, in accordance with at least one example of the present disclosure. As illustrated in FIG. 11, the lateral and medial condyle distal-most points 86, 87 can be shifted laterally distances 96, 102 from the lateral and medial condyle midpoints 90, 91, respectively. As described herein, distance 96 can substantially equal distance 102. Additionally, the trochlear groove 124 can be shifted laterally a distance 131 from axis 133. Axis 133 can extend from midpoint 132, which can be located halfway between the lateral and medial condyle midpoints 90, 91. Additionally, the lateral and medial dished surface portion distal-most points 163, 162 can be shifted laterally distances 166, 164 from the lateral and medial dished surface portion midpoints 161, 160. Distances 96, 102, 124, 166, and 164 can be substantially equal to each other, while the widths 92, 94 (as shown in FIG. 7B) of the lateral and medial condyles 66, 68 can be substantially equal to each other. As described herein, the lateralized trochlear groove 124 can provide a surgeon with an amount of lateralization before the femoral component itself is shifted laterally, and the surgeon can adjust or optimize patella tracking while reducing or minimizing implant overhang. Moreover, since the intercondylar box can remain centered between the condyles of equal width, the actual bone resection for the intercondylar box can be more central on the distal end of the femur as compared to a design with a centralized trochlear groove that would have to be shifted a greater distance laterally to achieve the same lateral position of the prosthetic trochlear groove on the distal femur.

A set including different sized femoral components 52, tibial components 136, or both can be provided, such as in a kit to allow for varying levels of lateralization. Particularly, the distance that the medial and lateral condyle distal-most points are shifted laterally from the medial and lateral condyle midpoints and the distance that the trochlear groove is shifted laterally from a midpoint centrally located between the medial and lateral condyle midpoints can vary. Additionally, the distance that the medial and lateral dished surface portion distal-most points are shifted laterally from the medial and lateral dished surface portion midpoints can vary. At least one of the femoral components 52 can include the medial and lateral condyle distal-most points shifted laterally from the medial and lateral condyle midpoints and the trochlear groove shifted laterally from the midpoint between the medial and lateral condyle midpoints. At least one of the tibial components 136 can include the medial and lateral dished surface portion distal-most points shifted laterally from the medial and lateral dished surface portion midpoints. In an example, at least one tibial component 134 that has the medial and lateral dished surface portion distal-most points shifted laterally from the medial and lateral dished surface portion midpoints can also include a tibial post that is located centrally between the medial and lateral dished surface midpoints.

Figure 12:
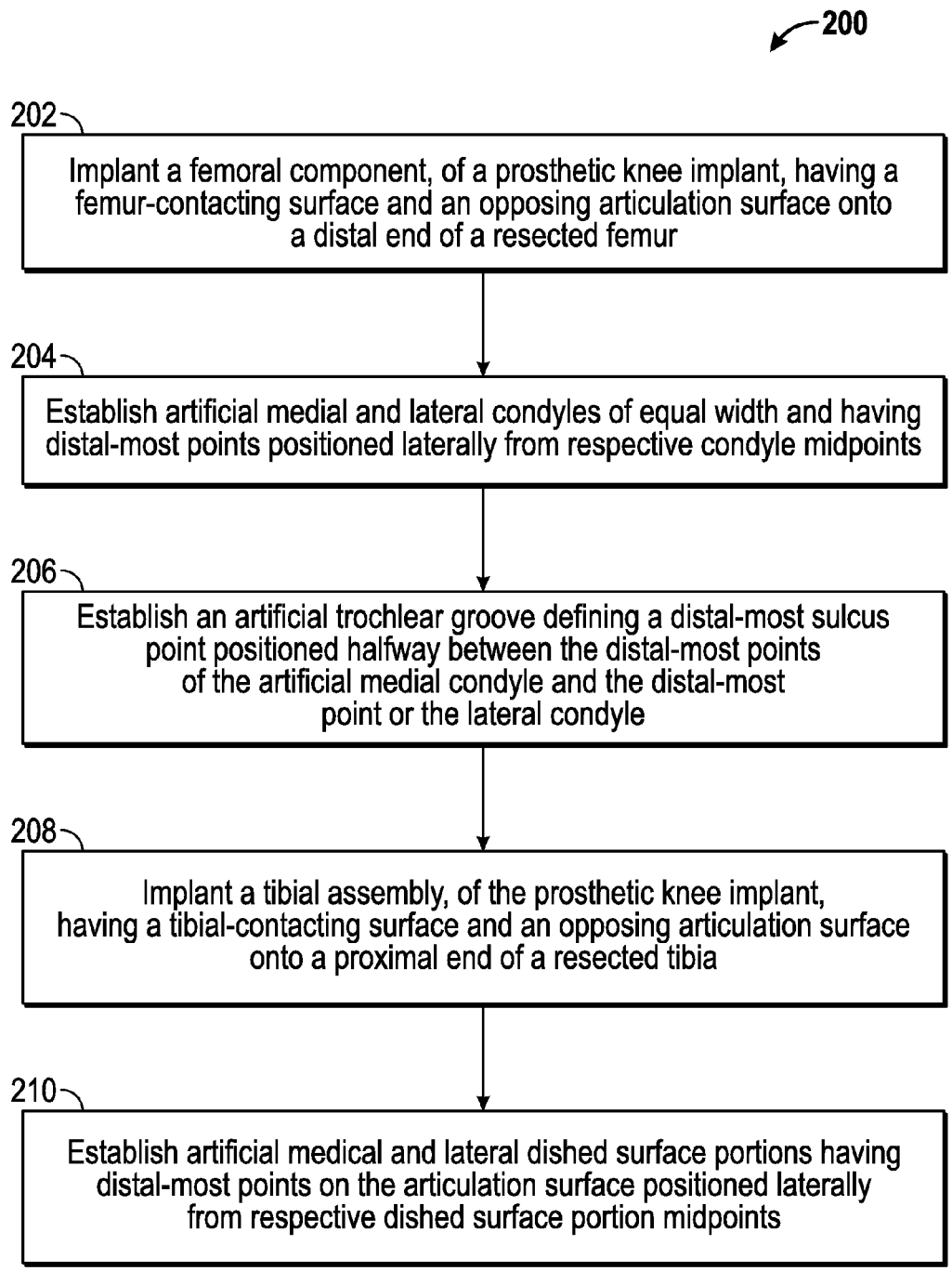
FIG. 12 illustrates a method of using a prosthetic knee implant, in accordance with at least one example of the present disclosure.

FIG. 12 illustrates a method 200 of using a prosthetic knee implant, in accordance with at least one example of the present disclosure. At 202, a surgeon can implant a femoral component of a prosthetic knee implant onto a distal end of a resected femur. The femoral component can include a femur-contacting surface and an opposing articulation surface. In an example, implanting the femoral component further can include establishing a box-like projection extending from the femur-contacting surface and located halfway between the medial condyle midpoint and the lateral condyle midpoint.

At 204, artificial medial and lateral condyles of equal width and having distal-most points located laterally from respective condyles midpoints can be established. In an example, establishing artificial medial and lateral condyles having distal-most points located laterally from the respective condyle midpoints can include lateralizing the distal-most points between 1.0 millimeter and 4.0 millimeters, inclusive, relative to the condyle midpoints.

As 206, an artificial trochlear groove that defines a distal-most sulcus point located halfway between the distal-most points of the artificial medial condyle and the distal-most point of the lateral condyle can be established. In an example, establishing the artificial trochlear groove includes lateralizing the distal-most sulcus point between 1.0 millimeter and 4.0 millimeters, inclusive, relative to a position halfway between the condyle midpoints.

At 208, a tibial component, of the prosthetic knee implant, having a tibial contacting surface and a tibial-contacting surface and an opposing articulation surface onto a proximal end of a resected tibia. In an example, implanting the tibial component can include establishing a tibial post extending from the articulation surface and located halfway between the medial dished surface portion midpoint and the lateral dished surface portion midpoint. Additionally, implanting the tibial component can include implanting a plate component, including the tibial-contacting surface, and a bearing component, including the articulation surface.

At 210, artificial medial and lateral dished surface portions having distal-most points on the articulation surface located laterally from respective dished surface portion midpoints can be established. In an example, establishing the artificial medial and lateral dished surface portions having distal-most points on the articulation surface located laterally from the respective dished surface portion midpoints can include lateralizing the distal-most points between 1.0 millimeter and 4.0 millimeters, inclusive, relative to the dished surface portion midpoints.

onto a distal end of a resected femur, including establishing artificial medial and lateral condyles of equal width and having distal-most points located laterally from respective condyle midpoints, and further establishing an artificial trochlear groove defining a distal-most sulcus point located halfway between the distal-most points of the artificial medial condyle and the artificial lateral condyle; and The above Detailed Description includes references to the accompanying drawings, which form a part of the Detailed Description. The drawings show, by way of illustration, specific embodiments in which the present tibial prosthesis systems, kits, and methods can be practiced. These embodiments are also referred to herein as "examples." While certain examples are shown and described with respect to a left knee or a right knee, it is to be appreciated that the present disclosure is equally applicable to both the left and right knees. All examples can also be used in partial or total knee replacement procedures.

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In the event of inconsistent usages between this document and any document so incorporated by reference, the usage in this document controls.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, "anterior" refers to a direction generally toward the front of a patient, "posterior" refers to a direction generally toward the back of the patient, "medial" refers to a direction generally toward the middle of the patient, and "lateral" refers to a direction generally toward the side of the patient. In this document, the phrase "anterior/posterior direction" is used to include an anterior to posterior direction or a posterior to anterior direction.

In the appended claims, the terms "including" and "in which" are used as the plain-English equivalents of the respective terms "comprising" and "wherein." The terms "including" and "comprising" are open-ended, that is, a system, kit, or method that includes elements in addition to those listed after such a term in a claim are still deemed to fall within the scope of that claim. Additionally, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A prosthetic knee implant, comprising:
    a femoral component having a femur-contacting surface, an opposing articulation surface, and proximal, distal, anterior and posterior portions, the femoral component including:
        a medial condyle and a lateral condyle, each of the condyles defining respective distal-most points and having substantially equal widths, as measured from a condyle medial side to a condyle lateral side and proximate the distal portion,
        the width of each of the condyles defining respective condyle midpoints halfway between the condyle medial sides and the condyle lateral sides, the distal-most points located laterally from the midpoints; and
        a trochlear groove, proximate the anterior portion, defining a distal-most sulcus point located halfway between the distal-most point of the medial condyle and the distal-most point of the lateral condyle.

2. The prosthetic knee implant of claim 1, wherein the distal-most point of the medial condyle is located laterally at a first distance from the medial condyle midpoint and the distal-most point of the lateral condyle is located laterally at a second distance, equal to the first distance, from the lateral condyle midpoint.

3. The prosthetic knee implant of claim 2, wherein the first distance and the second distance are between 1.0 millimeter and 4.0 millimeters, inclusive.

4. The prosthetic knee implant of claim 1, wherein the trochlear groove defines a patellar axis, when viewed from an anterior side of the femoral component, oriented substantially perpendicular to a plane connecting the distal-most point of the medial condyle and the distal-most point of the lateral condyle.

5. The prosthetic knee implant of claim 1, wherein the trochlear groove defines a patellar axis, when viewed from an anterior side of the femoral component, oriented substantially perpendicular to a plane connecting the medial condyle midpoint and the lateral condyle midpoint.

6. The prosthetic knee implant of claim 1, wherein the width of each of the condyles is between 19 millimeters and 31 millimeters, inclusive.

7. The prosthetic knee implant of claim 1, further comprising a box-like projection extending from the femur-contacting surface and located halfway between the medial condyle midpoint and the lateral condyle midpoint.

8. The prosthetic knee implant of claim 1, further comprising a concave surface extending between the medial and lateral condyles, the concave surface defining a proximal-most point halfway between the medial condyle distal-most point and the lateral condyle distal-most point.

9. The prosthetic knee implant of claim 1, further comprising a tibial component having a tibial-contacting surface, an opposing articulation surface, and proximal and distal portions.

10. The prosthetic knee implant of claim 9, wherein the articulation surface includes:
    a medial dished surface portion and a lateral dished surface portion, each of the dished surface portions defining respective distal-most points and widths, as measured from a surface portion medial side to a surface portion lateral side,
    the width of each of the dished surface portions defining respective dished surface portion midpoints halfway between the surface portion medial sides and the surface portion lateral sides, the distal-most points located laterally from the midpoints.

11. The prosthetic knee implant of claim 10, wherein the distal-most point of the medial dished surface portion is located laterally a third distance from the medial dished surface portion midpoint and the distal-most point of the lateral dished surface portion is located laterally a fourth distance, equal to the third distance, from the lateral dished surface portion midpoint.

12. The prosthetic knee implant of claim 11, wherein the distal-most point of the medial condyle is located laterally at a first distance from the medial condyle midpoint and the distal-most point of the lateral condyle is located laterally at a second distance, equal to the first distance, from the lateral condyle midpoint, and wherein the first and second distances are equal to the third and fourth distances.

13. The prosthetic knee implant of claim 10, wherein the medial dished surface portion and the lateral dished surface portion are asymmetrical, when viewed from a posterior side of the tibial component.

14. The prosthetic knee implant of claim 10, wherein the medial dished surface portion and the lateral dished surface portion are symmetrical, when viewed from a posterior side of the tibial component.

15. The prosthetic knee implant of claim 10, wherein the tibial component further comprises a tibial post extending from the articulation surface and located halfway between the medial dished surface portion midpoint and the lateral dished surface portion midpoint.

16. The prosthetic knee implant of claim 10, wherein the articulation surface further comprises a convex ridge surface extending between the medial and lateral dished surface portions, the convex ridge surface defining a proximal-most point halfway between the medial dished surface portion midpoint and the lateral dished surface portion midpoint.

17. The prosthetic knee implant of claim 10, wherein the tibial component includes a plate component, including the tibial-contacting surface, and a bearing component, including the articulation surface.

18. A method, comprising:
   implanting a femoral component, of a prosthetic knee implant, having a femur-contacting surface and an opposing articulation surface onto a distal end of a resected femur, including establishing artificial medial and lateral condyles of equal width and having distal-most points located laterally from respective condyle midpoints, and further establishing an artificial trochlear groove defining a distal-most sulcus point located halfway between the distal-most points of the artificial medial condyle and the distal-most point of the lateral condyle; and
   implanting a tibial component, of the prosthetic knee implant, having a tibial-contacting surface and an opposing articulation surface onto a proximal end of a resected tibia, including establishing artificial medial and lateral dished surface portions having distal-most points on the articulation surface located laterally from respective dished surface portion midpoints.

19. The method of claim 18, wherein establishing artificial medial and lateral condyles having distal-most points located laterally from the respective condyle midpoints includes lateralizing the distal-most points between 1.0 millimeter and 4.0 millimeters, relative to the condyle midpoints.

20. The method of any one of claim 18, wherein establishing the artificial trochlear groove includes lateralizing the distal-most sulcus point between 1.0 millimeter and 4.0 millimeters, relative to a position halfway between the condyle midpoints.

21. The method of any one of claim 18, wherein establishing the artificial medial and lateral dished surface portions having distal-most points on the articulation surface located laterally from the respective dished surface portion midpoints includes lateralizing the distal-most points between 1.0 millimeter and 4.0 millimeters, relative to the dished surface portion midpoints.

22. The method of any one of claim 18, wherein implanting the femoral component further includes establishing a box-like projection extending from the femur-contacting surface and located halfway between the medial condyle midpoint and the lateral condyle midpoint.

23. The method of any one of claim 18, wherein implanting the tibial component further includes establishing a tibial post extending from the articulation surface and located halfway between the medial dished surface portion midpoint and the lateral dished surface portion midpoint.

24. The method of any one of claim 18, wherein implanting the tibial component includes implanting a tibial plate component, including the tibial-contacting surface, and a bearing component, including the articulation surface.

* * * * *